(12) United States Patent
Simkin et al.

(10) Patent No.: US 7,090,691 B2
(45) Date of Patent: Aug. 15, 2006

(54) PHOTODYNAMIC THERAPY FOR THE TREATMENT OF HAIR LOSS

(75) Inventors: Guillermo O. Simkin, North Vancouver (CA); Anna M. Richter, Vancouver (CA); David W. C. Hunt, Surrey (CA); John Robert North, Vancouver (CA); Peter Lutwyche, Vancouver (CA); Ronald Erwin Boch, Vancouver (CA)

(73) Assignee: QLT Inc., Vancouver (CA)

( * ) Notice: Subject to any disclaimer, the term of this patent is extended or adjusted under 35 U.S.C. 154(b) by 129 days.

(21) Appl. No.: 10/291,795

(22) Filed: Nov. 8, 2002

(65) Prior Publication Data

US 2004/0015214 A1   Jan. 22, 2004

Related U.S. Application Data

(60) Provisional application No. 60/338,295, filed on Nov. 9, 2001.

(51) Int. Cl.
*A61N 5/06* (2006.01)

(52) U.S. Cl. .............................. 607/88; 607/91; 606/9; 128/898

(58) Field of Classification Search ............ 607/88–91, 607/94; 606/9; 128/898
See application file for complete search history.

(56) References Cited

U.S. PATENT DOCUMENTS

| 4,753,958 | A |   | 6/1988 | Weinstein et al. | 514/410 |
|---|---|---|---|---|---|
| 5,171,749 | A | * | 12/1992 | Levy et al. | 514/410 |
| 5,283,255 | A |   | 2/1994 | Levy et al. | 514/410 |
| 5,669,916 | A |   | 9/1997 | Anderson | 606/133 |
| 5,824,643 | A | * | 10/1998 | Pierce et al. | 514/12 |
| 5,871,480 | A |   | 2/1999 | Tankovich | 606/9 |
| 5,989,267 | A |   | 11/1999 | Anderson | 606/133 |
| 6,050,990 | A | * | 4/2000 | Tankovich et al. | 606/9 |
| 6,294,192 | B1 |   | 9/2001 | Patel et al. | 424/451 |
| 6,607,522 | B1 | * | 8/2003 | Hamblin et al. | 606/8 |
| 6,629,971 | B1 | * | 10/2003 | McDaniel | 606/9 |
| 6,676,655 | B1 | * | 1/2004 | McDaniel | 606/9 |
| 6,849,584 | B1 | * | 2/2005 | Geary et al. | 510/119 |
| 2003/0170822 | A1 | * | 9/2003 | Itoh | 435/69.4 |
| 2003/0199403 | A1 | * | 10/2003 | Wells et al. | 510/119 |
| 2004/0033493 | A1 | * | 2/2004 | Tchernev et al. | 435/6 |

FOREIGN PATENT DOCUMENTS

| EP | 0 350 036 | 1/1990 |
|---|---|---|
| EP | 1 147 785 | 10/2001 |
| FR | 2693906 | 1/1994 |
| WO | WO 88/05653 | 8/1988 |

(Continued)

OTHER PUBLICATIONS

Fiedler, V. and Alaiti, S., "Treatment of Alopecia Areata" Dermatologic Clinics 14(4):733-738 (1996).

(Continued)

*Primary Examiner*—A. Farah
(74) *Attorney, Agent, or Firm*—Morrison & Foerster LLP

(57) ABSTRACT

Photodynamic therapy (PDT) is used to stimulate and/or restore hair growth in areas of hair loss. Methods and compositions relating to PDT treatment for alopecia are disclosed. In light of PDT use to remove unwanted hair by inactivating or destroying hair follicles or destroying the tissue feeding the hair follicles, such methods and compositions relate to a surprising and unexpected discovery. PDT permits a means to treat conditions relating to hair loss such as androgenic alopecia, alopecia areata and drug-induced alopecia.

16 Claims, 3 Drawing Sheets

FOREIGN PATENT DOCUMENTS

| | | |
|---|---|---|
| WO | WO 95/07077 | 3/1995 |
| WO | WO 98/50387 | 11/1998 |
| WO | WO 99/59556 | 11/1999 |
| WO | WO 00/59475 | 10/2000 |
| WO | WO 00/64476 | 11/2000 |
| WO | WO 01/08660 | 2/2001 |
| WO | WO 01/85212 | 11/2001 |
| WO | WO 01/85213 | 11/2001 |

OTHER PUBLICATIONS

Lebwohl, M., "New Treatments for Alopecia Areata" Lancet 349:222-223 (1997).

McElwee, K. et al., "Comparison of Alopecia Areata in Human and Nonhuman Mammalian Species" Pathobiology 66(2):90-107 (1998).

Monfrecola, G. et al., "Topical Hematoporphyrin Plus UVA for Treatment of Alopecia Areata" Photodermatology 4:305-306 (1987).

Potapenko, A. and Kyagova, A., "The Application of Antioxidants in Investigations and Optimization of Photochemotherapy" Membr. Cell Biol. 12(2):269-278 (1998).

Sawaya, M.E., "Novel Agents for the Treatment of Alopecia" Seminars in Cutaneous Medicine and Surgery 17(4):276-283 (1998).

Shapiro, J., "Alopecia Areata; Update on Therapy" Dermatological Clinics 11(1):35-46 (1993).

Simkin, G. et al., "Inhibition of Contact Hypersensitivity with Different Analogs of Benzoporphyrin Derivative" Immunopharmacology 37:221-230 (1997).

Sundberg, J.P. et al., "Alopecia Areata in Aging C3H/HeJ Mice" Journal of Investigative Dermatology 102(6):847-856 (1994).

Tritrungtasna, O. et al., "Treatment of Alopecia Areata with Khellin and UVA" Correspondence- Int. J. Dermatol. 32(9):690 (1993).

Bissonnette, R. et al., "Current Status of Photodynamic Therapy in Dermatology" Dermatologic Clinics 15(3):507-519 (1997).

Lui, H. et al., "Photodynamic Therapy in Dermatology: Recent Developments" Dermatologic Clinics 11(1):1-13 (1993).

Delmarre, D. et al., "Aggregation Studies of Benzoporphyrin Derivative" Canadian Journal of Chemistry 79(5-6):1068-1074 (2001).

McCullough, J. et al., "Development of a Topical Hematoporphyrin Derivative Formulation: Characterization of Photosensitizing Effects In Vivo" Journal of Investigative Dermatology 81(6):528-532 (1983).

Sacchini, V. et al., "Topical Administration of Tetrasodium-Meso-Tetraphenyl-Porphinesulfonate (TPPS) and Red Light Irradiation for the Treatment of Superficial Neoplastic Lesions" Tumori 73(1):19-23 (1987).

Steiner, R. et al., "Rat Reproductive Performance Following Photodynamic Therapy with Topically Administered Photofrin" Human Reproduction 19(1):227-233 (1995).

Yarosh, D., "Liposomes in Investigative Dermatology" Photodermatology Photoimmunology & Photomedicine 17(5):203-212 (2001).

* cited by examiner

Figure 1.1
Figure 1.2
Figure 1.3
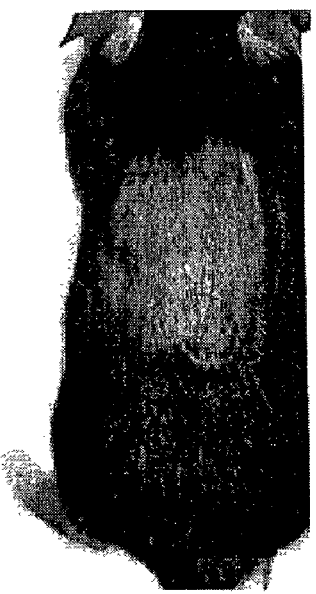
Figure 1.4
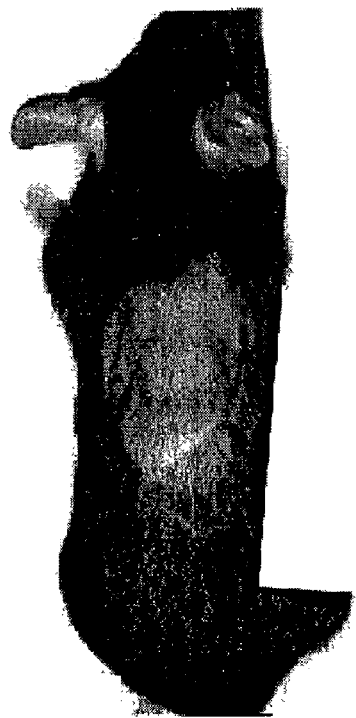

Figure 2.1
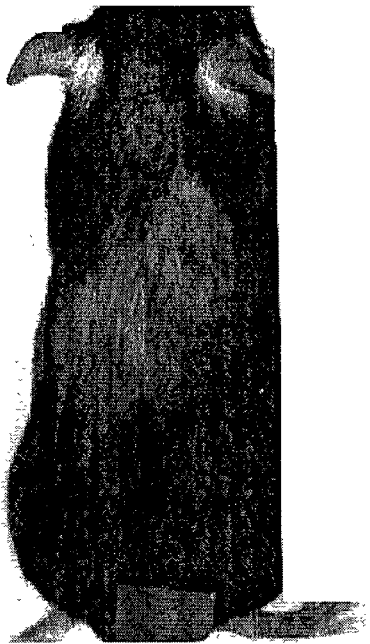
Figure 2.2
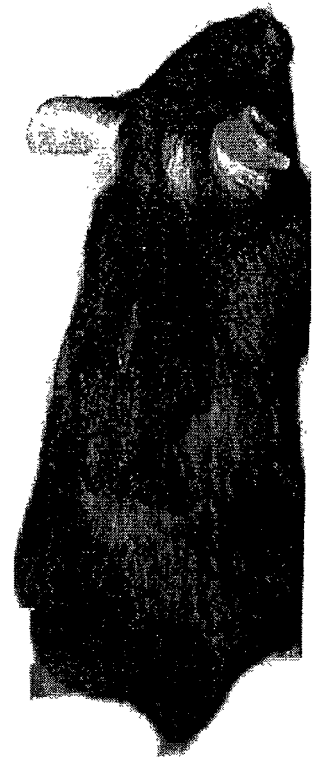
Figure 2.3
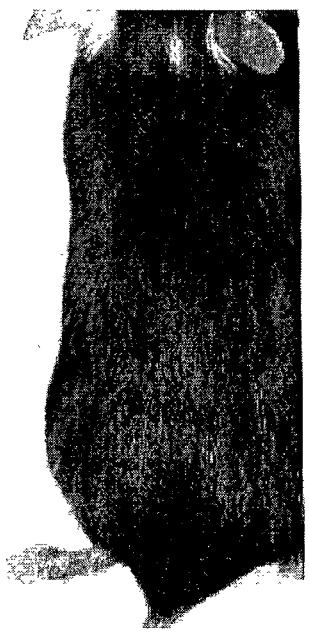
Figure 2.4
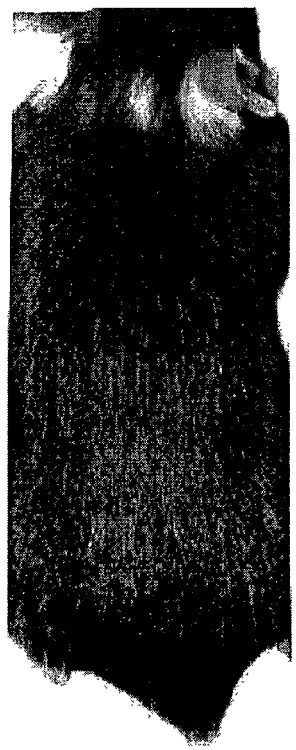

PHOTODYNAMIC THERAPY FOR THE TREATMENT OF HAIR LOSS

RELATED APPLICATIONS

This application claims benefit of priority from U.S. Provisional Application 60/338,295, filed Nov. 9, 2001, which is hereby incorporated in its entirety as if fully set forth.

FIELD OF THE INVENTION

This invention relates to the use of photodynamic therapy (PDT) and the use of PDT with appropriate photosensitizers to stimulate hair growth. In particular, the use of photosensitizers and PDT for treating conditions relating to hair loss, such as androgenetic alopecia and alopecia areata, is described.

BACKGROUND OF THE INVENTION

Alopecia is the general term referring to any disease or condition involving hair loss. There are several different types of hair loss, the most common being androgenetic alopecia (AGA; see Sawaya, M. E. *Seminars in Cutaneous Medicine and Surgery* 17(4):276–283, 1998), alopecia areata (AA; see Fiedler & Alaiti, *Dermatologic Clinics* 14(4): 733–738, 1996, as well as drug-induced alopecia.

Androgenetic alopecia (AGA) is a patterned, progressive loss of an excessive amount of hair from the scalp. Significant AGA occurs in 50% of men by the age of fifty and 50% of women by the age of sixty. AGA is believed to be a result of both genetic predisposition and the presence of a sufficient level of circulating androgens. It is thought that the enzyme 5 alpha reductase present in dermal papilla cells converts testosterone to dihydrotestosterone (DHT). DHT binds to androgen receptors, also localized in the dermal papilla cells, triggering changes in the hair follicle that result in (1) shortening of the anagen or growth phase of the hair cycle and lengthening of the telogen or hair regeneraton stage, (2) development of a latent phase in the hair cycle following shedding of the telogen hair, and (3) follicular miniaturization that reduces the calibre of the anagen hairs produced. It is thought that differential expression of 5-alpha reductase and/or androgen receptors in various types of hair follicles accounts for patterned hair loss.

The current treatments for AGA include minoxidil (Rogaine™), an anti-hypertensive drug for which the mechanism of action in promoting hair growth is unknown. Minoxidil must be applied topically on a daily basis, and is therefore somewhat inconvenient to use. Another drug used in the treatment of AGA is finasteride (Propecia™), a selective inhibitor of the type 2 isoenzyme 5-alpha reductase. This treatment has minimal efficacy, requires daily administration and has some anti-androgenic side effects such as alteration of libido. Hair transplants are also performed on the scalp of patients with hair loss associated with AGA, but these are prohibitively expensive for many people, and often require multiple time-consuming sessions to complete.

Alopecia areata (AA) has been reported to account for 2% of new outpatients in dermatology clinics (Fiedler & Alaiti supra). AA is a nonscarring form of hair loss which occurs in humans and other species and is thought to be due to an inflammatory reaction caused by autoimmune response directed against the anagen stage hair follicle structure (McElwee et al. *Pathobiology* 66(2): 90–107, 1998).

A number of therapeutic modalities have been tested for the treatment of AA, with variable results ranging from no effect to partial or full hair regrowth. In some cases chronic maintenance treatment is required. Major drawbacks of these treatments are side effects, which can be local or systemic in nature. Fiedler & Alaiti (supra) and Shapiro (*Dermatological Clinics* 11(1): 35–46, 1993) have reviewed the various treatments available for AA, including steroids (topical, intralesional and systemic), minoxidil, anthralin, photochemotherapy, cyclosporin A and other agents, as well as combination treatments.

Photochemotherapy therapy for AA using psoralen and high energy UVA (PUVA) treatment has met with very limited success and its effectiveness for AA is in doubt (Lebwohl, M. *Lancet* 349:222–223, 1997). Side effects of PUVA treatment such as nausea, pigmentary changes, risk of skin cancer formation, and cataracts have been reported (Fiedler & Alaiti, supra). Antioxidants have been used to ameliorate the side-effects of PUVA therapy (Ptapenko & Kyagova, *Membr. Cell Biol.* 12(2): 269–278, 1998). The use of 2% khellin, a compound with a chemical structure that resembles psoralen, and UVA for alopecia areata was found to be successful in 5 of the 10 patients tested (Orasa et al. *Int. J. Dermatol.* 32(9): 690, 1993). Since Khellin did not cause phototoxicity, the authors have suggested its use as an alternative to psoralen.

Hematoporphyrin and high energy UVA has been used in a very limited study by Monfrcola et al. (*Photodermatology* 4:305–306, 1987). Two patients were treated with topical hematoporphyrin (0.5%, HP) and UVA irradiation with three times a week for eight weeks. In the first week of treatment there was significant erythema and mild scaling followed by hyperpigmentation in the HP treated sites. Side effects included unpleasant reddish skin coloration for several hours and sometimes burning sensations during the irradiation phase. The authors point out that severe phototoxic reactions could occur with the use of HP concentrations greater than 1%. They also state that more work is needed before this approach can be subject to routine clinical use.

Photodynamic therapy (PDT) has been utilized for the removal of unwanted hair in human subjects. Briefly the treatment involves a topical application of a photosensitizer on a selected area of the skin, a period for absorption of the photosensitizer, followed by a pulse or continuous irradiation or vibration of the area. The process involves inactivating or destroying the hair follicles or destroying the tissue feeding the hair follicles (see U.S. Pat. Nos. 5,669,916; 5,871,480; WO 97/32046).

Photodynamic therapy is a minimally invasive two-step medical procedure that uses light-activated drugs called photosensitizers to treat a range of diseases involving rapid cell growth, such as cancerous tumors or abnormal blood vessels. First, a photosensitizer is administered and, once it has permeated the target tissue of interest, the photosensitizer is then activated by exposure to a pre-calculated dose of light at a particular wavelength. Once activated, the drug converts oxygen found in the cells into highly energized singlet oxygen. Singlet oxygen can react with subcellular components such as proteins and lipids, which disrupts normal cellular function and results in killing the cells. Lasers and fiber optics are used to deliver light.

There continues to be a need for a simple, rapid, and relatively side effect free method for stimulating and/or restoring hair growth in areas of hair loss.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

It has been discovered that photodynamic therapy (PDT) can stimulate hair growth and restore hair growth in areas of hair loss. In particular, PDT using a unique class of photosensitizer known as green porphyrins (Gp), in combination with irradiation, stimulates and/or restores hair growth with no apparent side effects. In light of the use of PDT to remove unwanted hair by inactivating or destroying hair follicles or destroying the tissue feeding the hair follicles, as discussed above, the instant invention relates to a surprising and unexpected discovery.

The instant invention also provides methods and compositions for treating lack of hair growth or a reduction or loss of existing hair by stimulating and/or restoring hair growth with PDT. Thus one aspect of the invention relates to methods for stimulating, inducing, restoring, reviving, renewing, replacing or otherwise activating hair growth in animals characterized by a lack of hair growth or a reduction in the amount of, or loss of, hair. In particular, the treatment methods of the invention comprise i) administering an effective and/or sufficient amount of photosensitizer resulting in an effective or desired degree of biodistribution; ii) irradiating at least a portion of the external surface of the animal with light including one or more wavelengths capable of activating said photosensitizer for a time period sufficient to activate the photosensitizer. The administrating and irradiating acts of (i) and (ii) may be repeated as necessary or desired to result in a desired level of hair growth.

The desired therapeutic response of hair growth can also be accomplished by the irradiation of skin, which has been treated with an effective amount of a photosensitizer, with light including one or more wavelengths capable of activating said photosensitizer for a time period sufficient to activate the photosensitizer and result in a desired level of hair growth. Moreover, the methods of the invention may be practiced with any photosensitizer, which may be delivered systemically or locally.

In another aspect, the invention is directed to formulations or compositions comprising photosensitizers for treating lack of hair growth or a reduction or loss of existing hair with the methods of the invention. The invention includes pharmaceutical compositions targeted to hair follicles, the surrounding tissue, or tissues which feed hair follicles. In particular, formulations comprising photosensitizers conjugated to agents, which specifically target or bind appropriate scalp or skin tissues, hair follicles, or tissues and cells surrounding said hair follicles, are preferred for use in the methods of the invention. Compositions comprising conjugated or unconjugated photosensitizers are optionally formulated with agents suitable or preferred for application to the scalp, or other skin where hair growth is desired. Examples of such agents include pharmaceutically acceptable carriers or excipients.

In addition to treatment of hair loss, the above described methods and compositions may be used for the stimulation of hair growth in areas not recognized as experiencing hair loss.

In preferred embodiments of the invention, the treatment methods and compositions comprise the use of a particularly potent group of photosensitizers known as green porphyrins, which are described in detail in Levy et al., U.S. Pat. No. 5,171,749 issued 15 Dec. 1992, which is incorporated herein by reference. The term "green porphyrins" refers to porphyrin derivatives obtained by reacting a porphyrin nucleus with an alkyne in a Diels-Alder type reaction to obtain a mono-hydrobenzoporphyrin. In particular, green porphyrin compounds such as benzoporphyrin derivative mono-acid (BPD-MA), EA6, and B3 may be used in the invention. Two preferred members of the green porphyrin family are verteporfin (comprising the 4 enantiomers shown below) and QLT 0074.

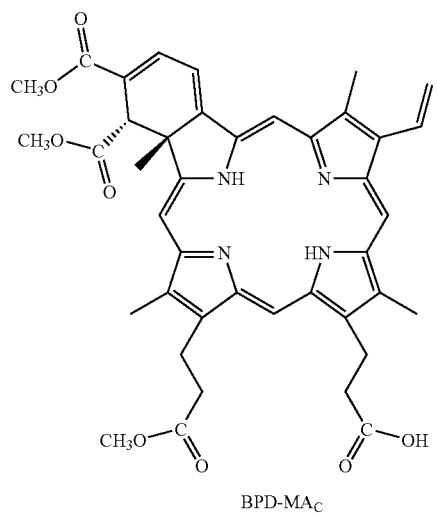

BPD-MA$_C$

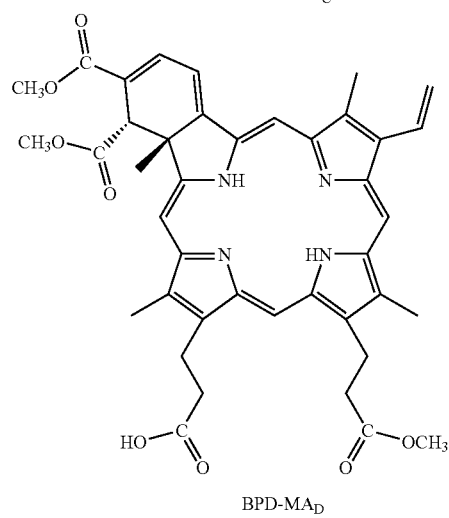

BPD-MA$_D$

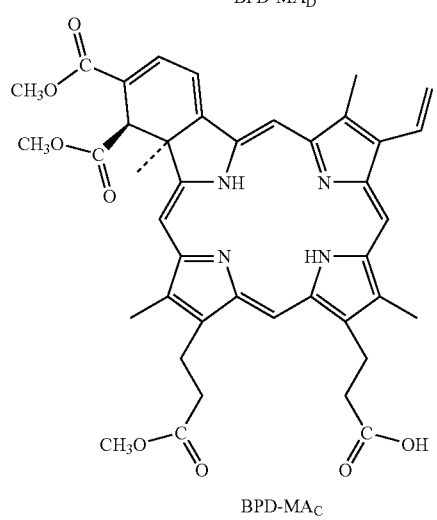

BPD-MA$_C$

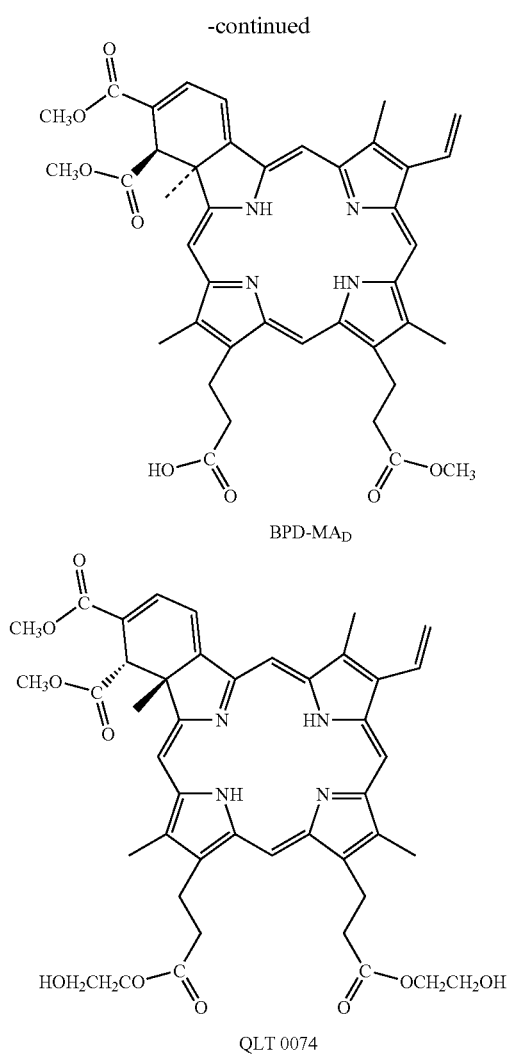

BPD-MA<sub>D</sub>

QLT 0074

Additionally, the methods of the invention preferably comprise irradiation with visible light absorbed by Gp.

BRIEF DESCRIPTION OF THE DRAWINGS

FIG. 1 shows photographs taken over time of a representative untreated control C57BL/6 mouse from an experiment examining the effect of photodynamic therapy (PDT) treatment of mice with alopecia of unknown etiology (Example 1). FIGS. 1.1 to 1.4 shows a control mouse with a worsening of the alopecic condition over the experimental period of 28 days.

FIG. 2 shows photographs taken over time of a representative PDT treated C57BL/6 mouse from the experiment examining the effect of PDT treatment on mice with alopecia of unknown etiology (Example 1). FIGS. 2.1 to 2.4 demonstrate that the PDT treatment over the experimental period of 28 days resulted in impressive hair growth in the alopecic patches.

DETAILED DESCRIPTION

Figure 3:
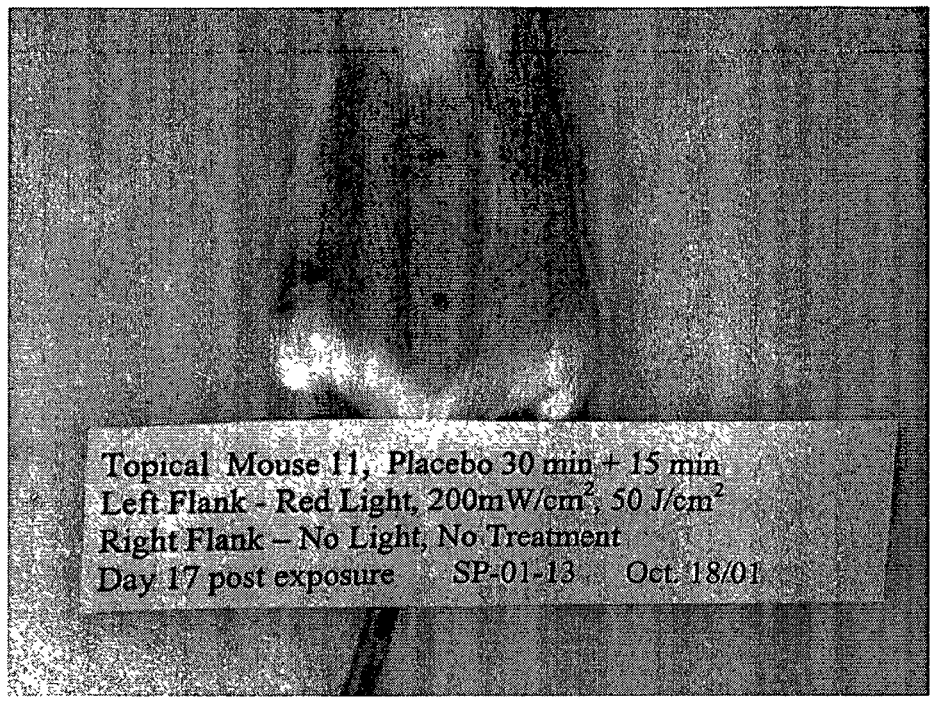
FIG. 3 is a photograph of a representative control Balb/c mouse that was shaved to remove hair, and subjected to a placebo PDT treatment (Example 2).

Briefly stated, the invention provides methods and compositions for stimulating hair growth utilizing photodynamic therapy (PDT) treatment. For example, one aspect of the invention includes methods for inducing or stimulating hair growth in animals characterized by reduction or loss of hair. A sample method would comprise: (a) administering an effective and/or sufficient amount of a photosensitizer capable of penetrating into target skin to result in an effective or desired degree of biodistribution; (b) irradiating the target skin with light comprising one or more wavelength capable of activating said photosensitizer for a time period sufficient to activate the photosensitizer; and optionally (c) repeating (a) and (b) as necessary or desired to elicit a desired level of hair growth. Such hair growth would be the desired therapeutic response in the majority of cases. PDT treatment of hair loss has the advantage that it obviates the need for daily administration of a drug.

The present invention may be used with any subject, vertebrate or invertebrate, capable of hair growth. Preferably, the invention is applied to skin tissue exhibiting, or suspected of, hair growth reduction or hair loss. Preferred subjects include mammals, with human subjects being particularly preferred.

After administration, the photosensitizer will be present in hair follicles and the surrounding tissues and cells for photoactivation. Irradiation, preferably with light of appropriate wavelength and intensity, will be applied using an appropriate light source, thereby activating the photosensitizer to stimulate and/or restore hair growth. By "stimulating" or "restoring" hair growth, all manner of inducing, reviving, renewing, replacing or otherwise activating hair growth are included. Preferably, the irradiation is with visible light or comprises a wavelength of visible light.

The formulations and methods of the invention generally relate to administering a photosensitizer, such as a green porphyrin, to a subject undergoing PDT for alopecia. A "Green porphyrin" (Gp) refers to a porphyrin derivative obtained by reacting a porphyrin nucleus with an alkyne in a Diels-Alder type reaction to obtain a mono-hydrobenzoporphyrin. Such resultant macropyrrolic compounds are called benzoporphyrin derivatives (BPDs), which is a synthetic chlorin-like porphyrin with various structural analogues, as shown in U.S. Pat. No. 5,171,749. Typically, green porphyrins are selected from a group of tetrapyrrolic porphyrin derivatives obtained by Diels-Alder reactions of acetylene derivatives with protoporphyrin under conditions that promote reaction at only one of the two available conjugated, nonaromatic diene structures present in the protoporphyrin-IX ring systems (rings A and B). Metallated forms of a Gp, in which a metal cation replaces one or two hydrogens in the center of the ring system, may also be used in the practice of the invention. The preparation of the green porphyrin compounds useful in this invention is described in detail in U.S. Pat. No. 5,095,030, which is hereby incorporated by reference as if fully set forth.

Preferably, the BPD is a benzoporphyrin derivative di-acid (BPD-DA), mono-acid ring A (BPD-MA), mono-acid ring B (BPD-MB), or mixtures thereof. These compounds absorb light at about 692 nm wavelength and have improved tissue penetration properties. The compounds of formulas BPD-MA and BPD-MB may be homogeneous, in which only the C ring carbalkoxyethyl or only the D ring carbalkoxyethyl would be hydrolyzed, or may be mixtures of the C and D ring substituent hydrolyzates. Some photosensitizers, such as phthalocyanines, may be used in high concentrations sufficient to offset their relatively slower uptake. An optimal photosensitizer for PDT treatment of alopecia should be rapidly taken up by hair follicles and/or the surrounding tissues and cells.

A particularly preferred photosensitizer formulation according to the present invention will satisfy the following general criteria: 1) it is capable of rapid entry into the target hair follicles and/or the surrounding tissues and cells; and 2) irradiation, preferably with light (and more preferably with visible light), results in the stimulation of and/or restoration of hair growth.

In one embodiment, the methods of the invention are used to stimulate and/or restore hair growth after initial diagnosis. In another embodiment, the methods of the invention follow other treatments for alopecia, including PDT, as a form of maintenance therapy to prevent appreciable hair loss and/or maintain hair growth. The latter may be used to prevent or inhibit the re-occurrence of alopecia. PDT may be used in conjunction with or in any combination with other treatments for alopecia, for example, such as Rogaine™, Propecia™ or hair transplants. For example, a patient may receive one or several PDT treatments, but also use Rogaine™ or Propecia™ as recommended.

The methods of the invention can be used to stimulate hair growth in any situation in which additional hair growth is desired. In particular, the methods of the invention will be useful when the subject has experienced loss of hair associated with a variety of conditions, including, but not limited to the following: anagen effluvium, drug-induced alopecia, radiotherapy, poisoning, diffuse alopecia areata, alopecia areata, loose anagen syndrome, postoperative occipital alopecia, syphilis, traction alopecia, tricholtillomania tinea capitis, telogen effluvium, telogen gravidarum, chronic telogen effluvium, early androgenentic alopecia, iron deficiency, malnutrition/malabsorption, hypothyroidism, hyperthyroidism, systemic lupus erythematosus, chronic renal failure, hepatic failure, advanced malignancy, viral or bacterial infection and androgenetic alopecia. In particular, the methods of the invention are useful for restoration of hair loss in androgenetic alopecia, alopecia areata, drug-induced alopecia (for example following chemotherapy treatment for cancer) and hair loss due to radiation treatment.

If the condition being treated is alopecia areata, preferably the photosensitizer pro-drug 5-ALA is not used for topical administration unless combined with at least one penetration enhancer that promotes the distribution of the drug within the hair follicles.

After administration of the photosensitizer, sufficient time is permitted to elapse for the compound to be taken up by the hair follicles and/or the surrounding tissues and cells. This time for uptake may be varied according to various parameters, including but not limited to the photosensitizer administered, the route of administration, the physiology of the subject and of the tumor cells, and the artisan's skill and experience. With green porphyrins, for example, the elapsed time may be from less than about one minute to more than three hours, preferably from one minute to three hours, and more preferably from 10 to 60 minutes. The cells, or tissues containing them, are then irradiated at the wavelength of maximum absorbance of the photosensitizer. In the case of BPDs, the wavelength is usually between about 550 and 700 nm, as discussed above. In particular, red light is advantageous because of its relatively lower energy and the resulting lack of toxicity it poses to normal tissue.

The compositions and methods of the present invention provide a useful PDT treatment to treat, and/or prevent or inhibit re-occurrence of, alopecia. The following describes exemplary photosensitizers, compositions and formulations of the present invention and their clinical application. Experimental data also are presented and described.

Photosensitizers

The methods of the invention may be practiced with a variety of photosensitizers. In addition to the above mentioned compounds, additional examples of photosensitizers useful in the invention for treatment of alopecia include, but are not limited to, green porphyrins disclosed in U.S. Pat. Nos. 5,283,255, 4,920,143, 4,883,790, 5,095,030, and 5,171,749; and green porphyrin derivatives, discussed in U.S. Pat. No. 5,880,145 and related U.S. patent application Ser. No. 09/265,245. Several structures of typical green porphyrins are shown in the above-cited patents, which also provide details for the production of the compounds. The invention may be practiced with a variety of synthetic and naturally occurring photosensitizers, including pro-drugs such as 5-aminolevulinic acid, porphyrins and porphyrin derivatives e.g. chlorins, bacteriochlorins, isobacteriochlorins, phthalocyanine and naphthalocyanines and other tetra- and poly-macrocyclic compounds, and related compounds (e.g. pyropheophorbides, sapphyrins and texaphyrins) and metal complexes (such as, but not limited by, tin, aluminum, zinc, lutetium). Tetrahydrochlorins, purpurins, porphycenes, and phenothiaziniums are also within the scope of the invention.

Particularly preferred photosensitizers include green porphyrins such as BPD-MA, EA6 and B3. Generally, any polypyrrolic or tetrapyrrolic macrocyclic photosensitive compound that is hydrophobic can be used in the invention. Examples of these and other photosensitizers for use in the present invention include, but are not limited to, angelicins; some biological macromolecules such as lipofuscin; photosystem II reaction centers; and D1-D2-cyt b-559 photosystem II reaction centers, chalcogenapyrillium dyes, chlorins, chlorophylls, coumarins, cyanines, ceratin DNA and related compounds, certain drugs such as adriamycin; afloqualone; amodiaquine; daunomycin; daunomycinone, certain flavins riboflavins, fullerenes, metalloporphyrins, metallophthalocyanines, methylene blue derivatives, naphthalimides, naphthalocyanines, certain natural compounds such as kynurenines; sanguinarine; berberine; carmane; and 5,7,9 (11),22-ergostatetraene-3 β-ol, nile blue derivatives, NSAIDs (nonsteroidal anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol.*, 70(4):391–475 (1999)).

Exemplary angelicins include those modified by aceto or methyl groups at the 3, 4', 4, 5', and/or 6 positions.

Exemplary chalcogenapyrillium dyes include pyrilium, selenopyrilium, thiopyrilium and telluropyrilium perchlorates.

Exemplary chlorins dyes include 5-azachlorin dimethyl ester derivative; 5,10,15,20-tetrakis-(m-hydroxyphenyl) bacteriochlorin; benzoporphyrin derivative monoacid ring A; benzoporphyrin derivative monoacid ring-A; porphine-2,18-dipropanoic acid, 7-[2-dimethyl-amino)-2-oxoethyl]-8-ethylidene-7,8-dihydro-3,7,12,17-tetramethyl, dimethylester; porphine-2,18-dipropanoic acid, 7-[2-dimethyl-amino)-2-oxoethyl]-8-ethylidene-8-ethyl-7,8-dihydro-3,7, 12,17-tetramethyl, dimethylester Z; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z ECHL; porphine-2,18-dipropanoic acid, 7-[2-dimethyl-amino)-2-oxoethyl]-8-ethylidene-8-n-heptyl-7,8-dihydro-3,7,12,17-tetramethyl, dimethylester Z; tin (II) porphine-2,18 -dipropanoic acid, 7-[2-(dimethyl-amino-2-oxoethyl]-8-ethylidene-8-n-heptyl-7,8-dihydro-3,7,12,17-tetramethyl, dimethylester Z; chlorin $e_6$; chlorin $e_6$ dimethyl ester; chlorin $e_6$ $k_3$; chlorin $e_6$ monomethyl ester; chlorin $e_6$ $Na_3$; chlorin $p_6$; chlorin $p_6$-trimethylester; chlorin derivative zinc (II) porphine-2,18-dipropanoic acid, 7-[2-(dimethy-lamino)-2-oxoethyl]-8-ethylidene-8-n-heptyl-7,8-dihydro-3,7,12,17-tetramethyl, dimethylester Z; $13^1$-deoxy-20-formyl-vic-dihydroxy-bacteriochlorin di-tert-butyl aspartate; $13^1$-deoxy-20-formyl-4-keto-bacteriochlorin di-tert-butyl aspartate; di-L-aspartyl chlorin $e_6$; mesochlo-rin; 5,10,15,20-tetrakis-(m-hydroxyphenyl) chlorin; meta-(tetrahydroxyphenyl)chlorin; methyl-$13^1$-deoxy-20-formyl-4-keto-bacteriochlorin; mono-L-aspartyl chlorin $e_6$; photoprotoporphyrin IX dimethyl ester; phycocyanobilin dimethyl ester; protochlorophyllide a; tin (IV) chlorin $e_6$; tin chlorin $e_6$; tin L-aspartyl chlorin $e_6$; tin octaethyl-benzochlo-rin; tin (IV) chlorin; zinc chlorin $e_6$; and zinc L-aspartyl chlorin $e_6$.

Exemplary chlorophylls dyes include chlorophylls a and b; bacteriochlorophylls a, b, c, or d; protochlorophylls; and amphiphilic derivatives thereof Exemplary coumarins include methoxycoumarins; thenoylcoumarins; khellin; RG 708; RG277; and visnagin.

Exemplary cyanines include benzoselenazole dye; benzoxazole dye; oxacarbocyanines; thiacarbocyanines; selenacarbocyanines; kryptocyanine; benzoxazole derivatives; quinoline derivatives; and merocyanines.

Exemplary fullerenes include $C_{60}$; $C_{70}$; $C_{76}$; dihydro-fullerenes; buckminster-fullerenes; and tetrahydro fullerenes.

Exemplary metalloporphyrins include chlorotexaphyrin nitrates; cadmium or cobalt or copper or Europium or gallium or lutetium or magnesium or manganese or nickel or palladium or platinum or samarium or silver or tin or zinc porphyrins, tetrabenzoporphyrins, porphines, texaphyrins, hematoporphyrins, tetrabenzoporphyrins, tetraphenylporphyrins, chlorotexaphyrins, porphyrazines; zinc protoporphyrin; and zinc protoporphyrin IX.

Exemplary metallophthalocyanines include aluminum chloroaluminum cobalt or copper or dichlorosilicon or gallium or germanium or lead or magnesium or nickel or palladium or ruthenium or silicon or tin or vanadium phthalocyanines (optionally sulfonates, disulfonates, trisulfonates, and tetrasulfonates).

Exemplary naphthalimides blue derivatives include N,N'-bis-(hydroperoxy-2-methoxyethyl)-1,4,5,8-naphthaldiim-ide; N-(hydroperoxy-2-methoxyethyl)-1,8-naphthalimide; 1,8-naphthalimide; N,N'-bis(2,2-dimethoxyethyl)-1,4,5,8-naphthaldiimide; and N,N'-bis(2,2-dimethylpropyl)-1,4,5,8-naphthaldiimide.

Exemplary naphthalocyanines include aluminum or silicon or zinc

Naphthalocyanines, chloronaphthalocyanines, t-butyl-naphthalocyanines, amidonaphthalocyanines, tetraaminon-aphthalocyanines, tetrabenzamidonaphthalocyanines, tetra-hexylamidonaphthalocyanines, tetramethoxy-benzamidonaphthalocyanines, tetramethoxynaphthalocyanines, naphthalocyanine tetrasul-fonates and tetradodecylamidonaphthalocyanines.

Exemplary nile blue derivatives include benzo[a]phe-nothiaziniums.

Exemplary perylenequinones include hypericins, calphostin C, cercosporins, elsinochromes, phleichromes and rubel-lin A.

Exemplary phenols include 2-benzylphenol; 2,2'-dihy-droxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl $13^1$-deoxy-20-formyl-7,8-vic-dihydro-bacterio-meso-pheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeuteroporphyrin IX dimethylester; dodecaphenylporphyrin; hematoporphyrin; hematoporphyrin IX; hematoporphyrin monomer; hematoporphyrin dimer; hematoporphyrin derivatives; hematoporphyrin IX dihydrochloride; hematoporphyrin IX dimethylester; meso-porphyrin dimethylester; monoformyl-monovinyl-deuteroporphyrin IX dimethylester; monohydroxyethylvinyl deuteroporphyrin; 5,10,15,20-tetra(o-hydroxyphenyl) porphyrin; 5,10,15,20-tetra(m-hydroxyphenyl) porphyrin; 5,10,15,20-tetrakis-(m-hydroxyphenyl) porphyrin; 5,10,15,20-tetra(p-hydroxyphenyl) porphyrin; 5,10,15,20-tetrakis (3-methoxyphenyl) porphyrin; 5,10,15,20-tetrakis (3,4-dimethoxyphenyl) porphyrin; 5,10,15,20-tetrakis (3,5-dimethoxyphenyl) porphyrin; 5,10,15,20-tetrakis (3,4,5-trimethoxyphenyl) porphyrin; 2,3,7,8,12,13,17,18-octaethyl-5,10,15,20-tetraphenylporphyrin; Photofrin®; Photofrin® II; porphyrin c; protoporphyrin; protoporphyrin IX; protoporphyrin dimethylester; protoporphyrin IX dimethylester; protoporphyrin propylaminoethylformamide iodide; protoporphyrin N,N-dimethylaminopropylformamide; protoporphyrin propylaminopropylformamide iodide; protoporphyrin butylformamide; protoporphyrin N,N-dimethylamino-formamide; protoporphyrin formamide; sapphyr tetrakis(4-sulfonatophenyl)porphyrin; meso-tetra(4-N-trimethylanilinium)-porphine; uroporphyrin; uroporphyrin IX; and uroporphyrin I.

Exemplary psoralens include methoxypsoralens dimethoxypsoralens; carbethoxypsoralens; pseudopsoralens; hydroxypsoralens; trimethylpsoralens; allopsoralens; isopseudpsoralen; acetoisopseudopsoralens; pseudoisopso-ralens; and acetopseudoisopsoralens.

Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

Exemplary quinones include anthraquinones; benzoquinones; hydroquinones; chlorohydroquinones; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary thiophenes include terthiophenes, bithiophenes, diphenylthiophene; quaterthiophenes; α-quaterthienyl; α-tetrathiophene; α-pentathiophene; α-hexathiophene; and α-heptathiophene.

Exemplary verdins include copro (II) verdin trimethyl ester; deuteroverdin methyl ester; mesoverdin methyl ester; and zinc methyl pyroverdin.

Exemplary vitamins include ergosterol (provitamin D2); hexamethyl-Co a Co b-dicyano-7-de(carboxymethyl)-7,8-didehydro-cobyrinate (Pyrocobester); pyrocobester; and vitamin D3.

Exemplary xanthene dyes include cosins and eosin derivatives, erythrosins, fluoresceins, phloxins, and rose bengals.

In one embodiment the preferred compounds for formulating are the highly hydrophobic tetrapyrrolic A and B-ring compounds, such as BPD-DA, -DB, -MA, and -MB. Most preferred are the B-ring compounds, BPD-MB, B-EA6, B-B3; the A-ring compounds BPD-MA, A-EA6 and A-B3; and dihydroxychlorins.

These compounds are porphyrin derivatives obtained by reacting a porphyrin nucleus with an alkyne in a Diels-Alder type reaction to obtain a monohydrobenzoporphyrin, and they are described in detail in the issued U.S. Pat. No. 5,171,749, which is hereby incorporated in its entirety by reference. Of course, combinations of photosensitizers may also be used. It is preferred that the absorption spectrum of the photosensitizer be in the visible range, typically between 350 nm and 1200 nm, more preferably between 400–900 nm, and even more preferably between 600–900 nm.

BPD-MA is described, for example, in U.S. Pat. Nos. 5,171,749 and 5,095,030; EA6 and B3 are described in U.S. Pat. Nos. 5,929,105 and 5,880,145, respectively, all of which are incorporated herein by reference. Preferred green porphyrins have the basic structure:

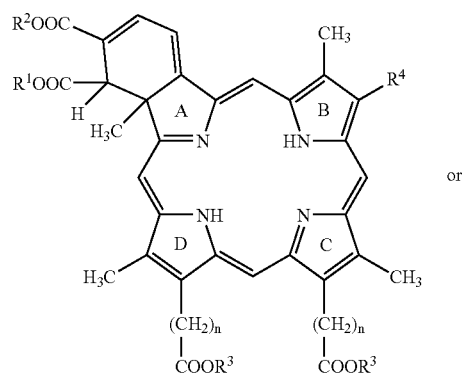

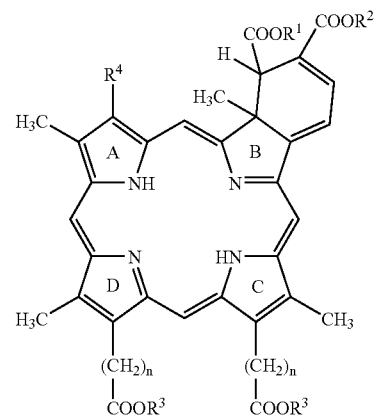

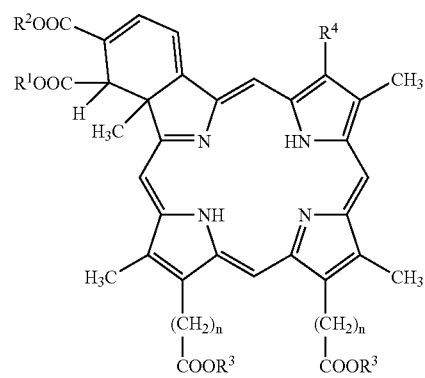

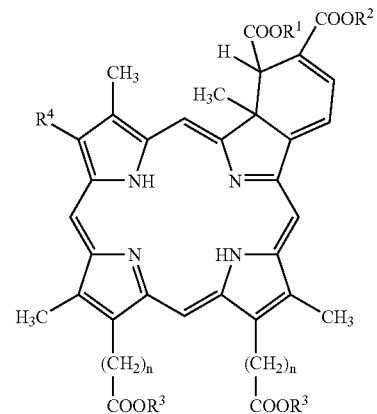

where $R^4$ is vinyl or 1-hydroxyethyl and $R^1$, $R^2$, and $R^3$ are H or alkyl or substituted alkyl, and n is an integer between 0 and 6, preferably 2.

BPD-MA (verteporfin) has the structure shown in formula 1 wherein $R^1$ and $R^2$ are methyl, $R^4$ is vinyl and one of $R^3$ is H and the other is methyl, and n=2. B-EA6 is of formula 2 wherein $R^1$ and R2 are methyl and both $R^3$ are 2-hydroxyethyl (i.e., the ethylene glycol esters). B3 is of formula 2 wherein $R^1$ is methyl, $R^2$ is H, and both $R^3$ are methyl, and n=2. In both EA6 and B3, $R^4$ is also vinyl.

The representations of BPD-MA$_C$ and BPD-MA$_D$, which are the enantiomeric components of verteporfin, as well as illustrations of A and B ring forms of EA6 and B3 (where n=2), are as follows:

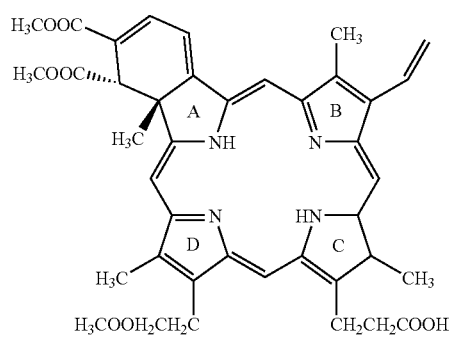

BPD-MA<sub>C</sub>

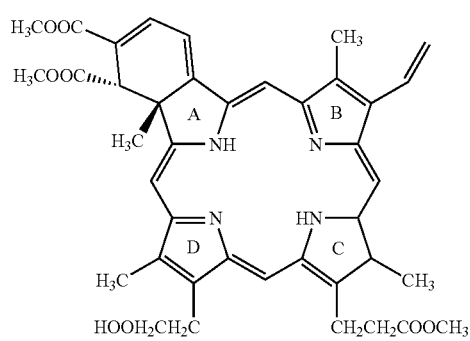

BPD-MA<sub>D</sub>

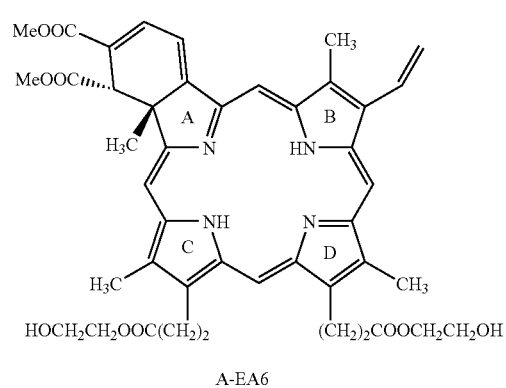

A-EA6

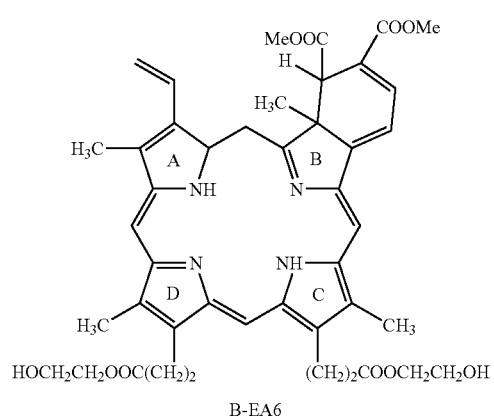

B-EA6

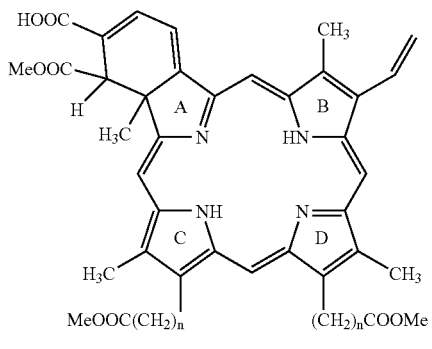

A-B3

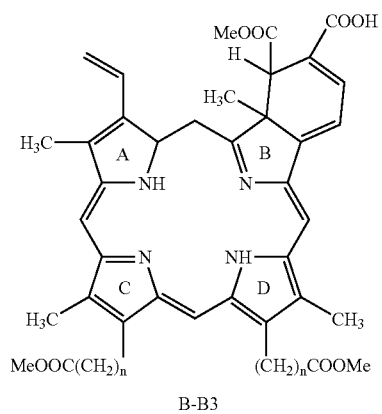

B-B3

Related compounds of formulas 3 and 4 are also useful; in general, $R^4$ will be vinyl or 1-hydroxyethyl and $R^1$, $R^2$, and $R^3$ are H or alkyl or substituted alkyl.

Additional examples of hydrophobic BPD B-ring compounds that are difficult to formulate, and are especially well suited to use in the invention are shown below. The compound QLT0069 is used in several of the Examples herein.

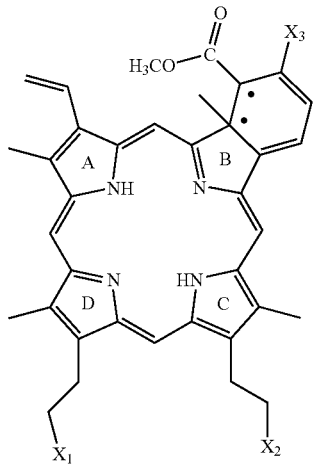

| Drug | X1 | X2 | X3 |
|---|---|---|---|
| QLT0060 | CO(O(CH$_2$)$_2$)OH | CO(O(CH$_2$)$_2$)OH | COOCH$_3$ |
| QLT0069 | COOCH$_3$ | COOCH$_3$ | COOH |
| QLT0078 | CO(O(CH$_2$)$_2$)$_2$OH | CO(O(CH$_2$)$_2$)$_2$OH | COOCH$_3$ |
| QLT0080 | CO(O(CH$_2$)$_2$)$_3$OH | CO(O(CH$_2$)$_2$)$_3$OH | COOCH$_3$ |
| QLT0081 | CO(O(CH$_2$)$_2$)$_2$OCH$_3$ | CO(O(CH$_2$)$_2$)$_2$OCH$_3$ | CO(O(CH$_2$)$_2$)$_2$OCH$_3$ |
| QLT0082 | CO(O(CH$_2$)$_2$)$_2$OH | CO(O(CH$_2$)$_2$)$_2$OH | CO(O(CH$_2$)$_2$)$_3$OH |
| QLT0083 | CO(O(CH$_2$)$_2$)$_3$OH | CO(O(CH$_2$)$_2$)$_3$OH | CO(O(CH$_2$)$_2$)$_3$OH |
| QLT0087 | CO(O(CH$_2$)$_2$)$_4$OH | CO(O(CH$_2$)$_2$)$_4$OH | COOCH$_3$ |
| QLT0088 | COOCH$_3$ | COOCH$_3$ | CONH(C$_6$H$_4$)(C$_5$H$_{10}$N) |
| QLT0090 | CO(O(CH$_2$)$_2$)$_5$OH | CO(O(CH$_2$)$_2$)$_5$OH | COOCH$_3$ |
| QLT0093 | CO(O(CH$_2$)$_2$)$_5$OH | CO(O(CH$_2$)$_2$)$_5$OH | CO(O(CH$_2$)$_2$)$_5$OH |

Dimeric forms of the green porphyrin and dimeric or multimeric forms of green porphyrin/porphyrin combinations may also be used. The dimers and oligomeric compounds of the invention can be prepared using reactions analogous to those for dimerization and oligomerization of porphyrins per se. The green porphyrins or green porphyrin/porphyrin linkages can be made directly, or porphyrins may be coupled, followed by a Diels-Alder reaction of either or both terminal porphyrins to convert them to the corresponding green porphyrins.

Other non-limiting examples of photosensitizers which may be useful in the invention are photosensitizing Diels-Alder porphyrin derivatives, described in U.S. Pat. No. 5,308,608; porphyrin-like compounds, described in U.S. Pat. No. 5,405,957, 5,512,675, and 5,726,304; bacteriochlorophyll-A derivatives described in U.S. Pat. Nos. 5,171,741 and 5,173,504; chlorins, isobacteriochlorins and bacteriochlorins, as described in U.S. Pat. No. 5,831,088; meso-monoiodo-substituted and meso substituted tripyrrane, described in U.S. Pat. No. 5,831,088; polypyrrolic macrocycles from meso-substituted tripyrrane compounds, described in U.S. Pat. Nos. 5,703,230, 5,883,246, and 5,919,923; and ethylene glycol esters, described in U.S. Pat. No. 5,929,105. All of the patents cited in this paragraph are hereby incorporated by reference as if fully set forth. Generally any hydrophobic photosensitizers, which absorb in the ultra-violet, visible and infra-red spectroscopic ranges would be useful for practicing this invention.

Additionally, the photosensitizers used in the invention may be conjugated to various ligands to facilitate targeting to hair follicles or the surrounding tissues and cells. These ligands include those that are receptor-specific as well as immunoglobulins and fragments thereof Preferred ligands include antibodies in general and monoclonal antibodies, as well as immunologically reactive fragments of both.

The photosensitizers of the invention may be administered as a single compound or as a mixture of various photosensitizers. Suitable formulations include those appropriate for administration of therapeutic compounds in vivo. Additionally, other components may be incorporated into such formulations. These include, for example, visible dyes to facilitate visualization or imaging of the formulation or various enzymes to facilitate the access of a photosensitizing compound to target sites.

Formulations

The photosensitizers of the invention may be formulated into a variety of compositions. These compositions may also comprise further components, such as conventional delivery vehicles and excipients including isotonising agents, pH regulators, solvents, solubilizers, dyes, gelling agents and thickeners and buffers and combinations thereof. Appropriate formulations and dosages for the administration of photosensitizers are known in the art. Suitable excipients for use with photosensitizers include water, saline, dextrose, glycerol and the like.

Typically, the photosensitizer is formulated by mixing it, at an appropriate temperature, e.g., at ambient temperatures, and at appropriate pHs, and the desired degree of purity, with one or more physiologically acceptable carriers, i.e., carriers that are nontoxic at the dosages and concentrations employed. Generally, the pH of the formulation depends mainly on the particular use, and concentration of photosensitizer, but preferably ranges anywhere from about 3 to about 8. Preferably, the photosensitizer is maintained at a pH in the physiological range (e.g., about 6.5 to about 7.5). The presence of salts is not necessary, and, therefore the formulation preferably is not an electrolyte solution.

The particular concentration of a given photosensitizer should be adjusted according to its photosensitizing potency. For example, BPD-DA can be used but at about a five-fold higher concentration than that of BPD-MA. Moreover, the Gp may be solubilized in a different manner than by formulation in liposomes. For example, stocks of BPD-MA or any other Gp may be diluted in DMSO (dimethylsulfoxide), polyethylene glycol (PEG) or any other solvent acceptable for use in the treatment of skin tissues and cells. In some embodiments of the invention the formulations will contain one or more PEGs of different molecular weights. Formulations comprising at least one PEG of less than about 2000, less than about 1500, less than about 1000, less than about 800, less than about 600, less than about 500, less than about 400, less than about 200, and less than about 100 molecular weight are used in the formulations of the invention. A second PEG of about 3000, about 3350, about 3500, or about 4000 or higher molecular weight may also be included.

Normally, the adjustment of pH is not required when liposomal formulations are used, as both components have a neutral pH. However, when solvents other than liposomes are used, the pH may require adjustment before mixing the Gp with the other material.

Preparation of dry formulations that are reconstituted immediately before use also are contemplated. The preparation of dry or lyophilized formulations of the compositions of the present invention can also be effected in a known manner, conveniently from the solutions of the invention. The dry formulations of this invention are also storable. By conventional techniques, a solution can be evaporated to dryness under mild conditions, especially after the addition of solvents for azeotropic removal of water, typically a mixture of toluene and ethanol. The residue is thereafter conveniently dried, e.g. for some hours in a drying oven.

Suitable isotonising agents are preferably nonionic isotonising agents such as urea, glycerol, sorbitol, mannitol, aminoethanol or propylene glycol as well as ionic isotonising agents such as sodium chloride. The solutions of this invention will contain the isotonising agent, if present, in an amount sufficient to bring about the formation of an approximately isotonic solution. The expression "an approximately isotonic solution" will be taken to mean in this context a solution that has an osmolarity of about 300 milliosmol (mOsm), conveniently 300+10% mOsm. It should be borne in mind that all components of the solution contribute to the osmolarity. The nonionic isotonising agent, if present, is added in customary amounts, i.e., preferably in amounts of about 1 to about 3.5 percent by weight, preferably in amounts of about 1.5 to 3 percent by weight.

Solubilizers such as cremophor types, preferably Cremophor RH 40, Transcutol®, corn glycerides or Tween types or other customary solubilisers, may be added to the solutions of the invention in standard amounts.

A further preferred embodiment of the invention relates to a solution comprising a Gp, and a partially etherified cyclodextrin, the ether substituents of which are hydroxyethyl, hydroxypropyl or dihydroxypropyl groups, a nonionic isotonising agent, a buffer and an optional solvent. However, appropriate cyclodextrins should be of a size and conformation appropriate for use with the photosensitizing agents disclosed herein.

Summaries of pharmaceutical compositions suitable for use with the instant photosensitizers are known in the art and are found, for instance, in *Remington's Pharmaceutical Sciences*. Preferred for the practice of the invention are pharmaceutical excipients or carriers capable of directing the photosensitizer to the area of hair growth reduction or hair loss. In the case of topical formulations (including ointments), penetration enhancers such as Transcutol® (diethylene glycol monoethyl ether) are highly desirable in order to promote the distribution of photosensitizer in the hair follicle and surrounding tissues. In particular if the condition being treated is alopecia areata, preferably the photosensitizer pro-drug 5-ALA or similar drugs are not used for topical administration unless combined with at least one penetration enhancer that promotes the distribution of the drug within the hair follicles and surrounding tissues.

Administration of Photosensitizers

As noted above, the treatment methods of the invention are targeted to hair follicles and/or surrounding tissues and cells as a treatment for alopecia. The photosensitizer containing preparations of the invention may be administered systemically or locally and may be used alone or as components of mixtures. The route of administration for the photosensitizer may be topical, intravenous, oral, or by use of an implant. For example green porphyrins may be administered by means including, but not limited to, topical-preparations, intravenous injection or infusion, oral intake, or local administration in the form of intradermal injection or an implant. Additional routes of administration are subcutaneous, intramuscular, or intraperitoneal injections of the photosensitizers in conventional or convenient forms.

In particular, liposomal or lipophilic formulations are most desirable, and topical delivery of photosensitizers is preferred, while injection may also be used when desired. For topical administration, the photosensitizers may be in standard topical formulations and compositions including lotions, suspensions or pastes. Oral administration of suitable formulations may also be appropriate in those instances where the photosensitizer may be readily administered to the hair follicle and/or surrounding tissues or cells via this route. A preferred method of administration is to apply the photosenisitizer topically in an excipient containing solubilizing agent, such as Cremophor or corn glycerides, and to wash the treatment area within about an hour (such as, but not limited to, after about 10, about 15, about 20, about 30, about 45, or about 60 minutes) with the excipient to remove excess drug from the surface of the skin.

The dose of photosensitizers may be optimized by the skilled artisan depending on factors such as, but not limited to, the photosensitizer chosen, the physical delivery system in which it is carried, the individual subject, and the judgment of the skilled practitioner. It should be noted that the various parameters used for effective PDT in the invention are interrelated. Therefore, the dose should also be adjusted with respect to other parameters, for example, fluence, irradiance, duration of the light used in PDT, and time interval between administration of the dose and the therapeutic irradiation. All of these parameters may be readily adjusted using routine experimentation to produce a desired level of alopecia treatment without causing significant damage to the surrounding tissue. With photosensitizers, for example, the form of administration, such as in liposomes or when coupled to a target-specific ligand, such as an antibody or an immunologically active fragment thereof, is one factor considered by a skilled artisan.

Depending on the specificity of the preparation, smaller or larger doses of photosensitizers may be needed. For compositions which are highly specific to the target skin tissues and cells, such as those with the photosensitizer conjugated to a highly specific monoclonal antibody preparation or specific receptor ligand, dosages in the range of 0.005–10 mg/kg of body weight are suggested for systemic administration. For compositions which are less specific to the target, larger dosages, up to 1–20 mg/kg, may be desirable. The potency of the photosensitizer also determines the dosage, with less required for highly potent photosensitizers, and more for photosensitizers with less potency. The preferred range for use in mice is from about 0.05 mg/kg to about 20 mg/kg. The useful range in humans for the photosensitizer will be lower than mice, such as from about 0.005 mg/kg to about 4 mg/kg, and preferably from about 0.05 to about 2.0 mg/kg.

For topical formulations (such as ointments) to be applied to the surface of the skin, the concentration of the photosensitizer in the excipient can range from about 0.001 to about 10% w/w, and more preferably from about 0.005 to about 5% w/w (or about 0.05 to about 1% w/w), and even more preferably between about 0.1 to about 1% w/w. Particularly preferred is the use of a 0.2% (or about 0.2) w/w topical formulation. The foregoing ranges are merely suggestive in that the number of variables with regard to an individual treatment regime is large and considerable deviation from these values may be expected.

If the photosensitizer is a green porphyrin, topical formulations to be applied to the skin containing in the range from about 0.005% (w/w) to about 0.5% (w/w), are particularly preferred for stimulating hair growth. Higher concentrations, in the range of about 0.5% (w/w) to 5% may also be used, but have the disadvantage that they require more green porphyrin to manufacture. Lower doses, in the range from about 0.0005 to about 0.005 may also be used, but may require longer irradiation treatment times. A topical formulation containing 0.2% (w/w) of QLT 0074 was shown to be localized in human hair follicles thirty minutes after application to human cadaver scalp skin.

The skilled artisan is free to vary the foregoing concentrations so that the uptake and stimulation/restoration parameters are consistent with the therapeutic objectives disclosed above. The concentration of a particular photosensitizer to use in a topical formulation can easily be determined by performing a dose ranging study similar to the one outlined in the Examples below.

Each photosensitizer requires activation with an appropriate wavelength(s) of radiation. As such, the methods of the invention may be conducted with any irradiation, preferably with light, which activates the photosensitizer used. Preferably, the irradiation contains one or more wavelength which is capable of penetrating the skin to activate the photosensitizer used. The wavelength(s) of radiation or light useful in the invention depends on the activation range of the photosensitizer used as part of the treatment method. Wavelengths of about 380–900 nanometers (nm) are preferred, depending upon the photosensitizer and upon the depth of tissue penetration desired. More preferred are wavelengths from about 400 to about 900 nm, most preferred from about 400 to about 700 nm. For example, BPD-MA, a green porphyrin derivative, can be activated by red and blue light as well as ambient light containing wavelengths from 400–900 nm. Light having a wavelength shorter than 400 nm is acceptable, but not preferred because of the potentially damaging effects of UVA light.

An appropriate light source, preferably a laser or light emitting diode (LED), in the range of about 550 to about 900 nm, depending on the absorption spectrum of the photosensitizer, may be used for photosensitizer activation An appropriate and preferred wavelength for such a laser includes 690±12.5 nm at half maximum when BPDs are used. .

Alternatively any convenient source of light having a component of wavelengths that are absorbed by the photosensitizer may be used, for example, an operating room lamp, or any bright light source, including sunlight. Light wavelengths in the ultraviolet range should, however, generally be avoided because of their mutagenic potential. The light dose administered during the PDT treatment contemplated herein can vary, and can range between about 0.1 to about 200 J/cm$^2$. Increases in irradiance will generally decrease the light exposure times. Generally, a higher dose of photosensitizer will decrease the light dose required to exert a therapeutic effect.

Normally, the intensity of the light source should not exceed about 600–1000 mW/cm$^2$. Irradiances between about 50 and 400 mW/cm$^2$, and more preferably between 100 and 200 mW/cm$^2$ are preferred. The total dose of the irradiation should generally not exceed 200 J/cm$^2$, and is preferably at or about 25, 50, 75, 100, 125, 150, or 175 J/cm$^2$. Preferably, for photosensitizers of high potency, such as green porphyrins the dosage of the light is about 5–50 J/cm$^2$ for systemically-delivered drug and about 25–200 J/cm$^2$ for topically-delivered photosensitizers. Normally, the irradiation lasts from about 10 seconds to about 3 hours, and preferably between about 5 minutes and 1 hour. Irradiation times of about 10, about 15, about 20, about 30, about 45, about 60, about 75, about 90, about 105, about 120, about 135, about 150, about 165 and about 180 minutes may be used.

The irradiation or light exposure used in the invention may be directed to a localized area, such as the eyebrow area of a human, or to cover an extended portion of the body or scalp depending on the alopecic patch to be treated. Treatment may be preceded with an assessment of the time of light exposure for the patient's minimal erythemal dose (MED) occurrence in order to avoid potential burning of the exposed skin. Such treatments may be at a frequency of one to three treatments on a weekly, biweekly, monthly, bimonthly, quarterly, biannually, or annually, or other suitable time interval to stimulate hair growth or to maintain the prevailing condition. In cases where hair loss is observed, maintenance treatment on a regular basis may be initiated and sustained.

The number of applications of PDT treatment may depend on the type and the extent of alopecia condition as well as the experience of those in the art and the condition of the subject. Preferably, the PDT treatment is repeated at a frequency of 1, 2, 3, 4, 5, 6, or 12 times per 3 month period.

Light treatment can take place at any time following administration of photosensitizer as long as the photosensitizer has not been completely cleared from the skin. Light treatment within a period of about five minutes to about 6 hours after administration of the photosensitizer is generally preferred, with a range of 30 minutes to 2 hours being especially preferred. Irradiation times of about 15, about 30, about 45, about 60, about 75, about 90, about 105, and about 120 minutes may be used. The time between administration of photosensitizer and administration of light will vary depending on the pharmacokinetics of the photosensitizer used. Photosensitizers that rapidly accumulate in target tissues can be activated soon after administration. Photosensitizers that are cleared from tissues quickly should be activated soon after accumulation in the target tissues.

Having now generally described the invention, the same will be more readily understood through reference to the following examples which are provided by way of illustration, and are not intended to be limiting of the present invention, unless specified.

EXAMPLE 1

Photodynamic Therapy Treatment of C57BL/6 Mice with Alopecia of Unknown Etiology C57BL/6 mice used in this example were purchased from Jackson Laboratories (Bar Harbor, Me.). After 4 weeks of housing some of the C57BL/6 mice spontaneously developed a hair loss condition which resulted in large bald patches (see FIG. 1.1) at 12 to 14 weeks of age. One of these animals was sacrificed and skin samples were sent for histopathological evaluation. The skin sample showed no evidence of infection according to a veterinarian's histopathological examination. The condition was diagnosed as alopecia of unknown etiology. The presence of an undefined "mononuclear cell infiltrate" was noted within the affected skin and, without being bound by theory, may indicate an autoimmune etiology for alopecia in the mouse.

Eight mice that were developing hair loss were chosen. Four mice were randomly picked for the PDT treatment while the remaining four served as untreated controls. PDT consisted of intravenously injecting vertporfin in a lipid-based formulation (Visudyne®, Novartis Opthalmics, Duluth, Ga.) at a dosage of 1 mg/kg of body weight per mouse, followed by exposure to 690 nm wavelength red light at 15 J/cm$^2$, delivered by an array of light emitting diode (LED) panels, at 1 hour post-injection. (see Simkin G. et Al. 1997. Inhibition of contact hypersensitivity with different analogs of benzoporphyrin derivative. *Immunopharmacology* 37:221–230, which is incorporated by reference as if fully set forth). This was followed by two additional PDT treatments on days 7 and 14.

The mice were observed and photographed on days 0, 13, 21 and 28. FIGS. 1 and 2 show a representative untreated control and a PDT treated mouse photographed at day 0, day 13, day 21 and day 28. There was no improvement in the alopecic patches in the untreated control group of mice (n=4) and in fact, these patches worsened over the time course of the experiment (FIGS. 1.1 to 1.4). In the PDT treated group (n=4) there was a startling and impressive hair growth observed in the alopecic patches after the first and second treatments as demonstrated in FIGS. 2—2 and 2–3. By day 28, the previously alopecic patches were covered with what appeared to be a full complement of hair.

EXAMPLE 2

PDT-induced Stimulation of Hair Growth using Topically-applied Photosensitizer

To prepare QLT 0074-containing ointment, QLT 0074 photosensitizer was dissolved in glacial acetic acid to solubilize it. The solution was then frozen in a dry ice/isopropanol bath and the acetic acid was removed by lyophilization. The resultant material was a fine fluffy powder. Analytical testing of the cryodessicated QLT 0074 indicated that the process did not cause degradation. The ointment base was prepared by first warming polyethylene glycol 200 (PEG 200) to 80–90° C. with stirring. Polyethylene glycol 3350 (PEG 3.35K) was then added with stirring, followed by oleyl alcohol, and then diethylene glycol monoethyl ether. Stirring was continued until the solution was clear. The ointment base was cooled to approximately 50° C., and the QLT 0074 was added with stirring. Stirring was continued as the mixture cooled, until a homogenous paste was achieved. The ointment contained the following proportions of the components on a weight/weight basis.

QLT 0074 (1)
PEG-200 (108)
diethylene glycol monoethyl ether Transcutol® (40)
PEG-3.35K (32)
oleyl alcohol (20).

The concentration of QLT 0074 in the ointment was 0.5% weight/weight. A placebo ointment was prepared which contained the excipients, but lacked QLT 0074. The ointments were stored refrigerated at 2 to 8° C. until use.

Female Balb/C mice (8–14 weeks old) were supplied by Charles River Canada (St. Constance, Quebec). Mice were acclimated to laboratory conditions for seven days prior to release from quarantine. Cages of animals were held in enclosed ventilated animal racks in temperature and humidity controlled rooms. Mice were kept on a standard diet and water ad libitum in a 12 hours light/dark cycle. Mice were randomly assigned to PDT treatment and controlled groups, and were monitored for pain or distress.

Eighteen mice were shaved to remove hair from the back and both flanks. The right side of each mouse served as a control, receiving no light and no photosensitizer. QLT 0074-containing ointment was applied to a square spot on the left side of each of mice 1–9 using a square template, with the same quantity of ointment applied to each spot. Placebo formulation was applied to a square spot on the left side of each of mice 10–18 in the same manner. After 30 minutes, the excess ointment was removed from the spots by washing with water using a sterile gauze pad, and then placebo ointment was applied to the same spots on each of mice 1–18. After 15 minutes, the spots were irradiated with 50J/cm$^2$ of light delivered at a fluence rate of 200 mW/cm$^2$. Light (688 nm +/−6 nm) was delivered from a light emitting diode (LED) unit (Quantum, Model QB-Quanta-Med-688).

Figure 4:
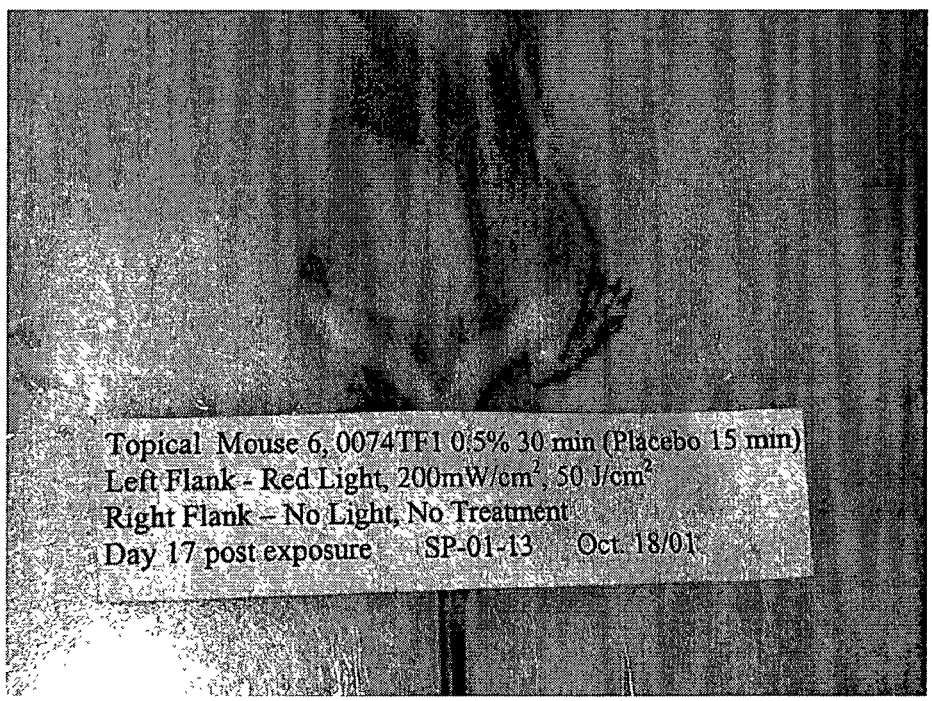
FIG. 4 is a photograph of a representative shaved Balb/c mouse that was shaved to remove hair, and subjected to a PDT treatment using the photosensitizer QLT 0074 (Example 2). Hair re-growth was observed 17 days after PDT treatment.

Out of the nine mice treated with QLT 0074, five developed hair growth on the treated area by day 17. In contrast, none of the placebo-treated mice developed hair regrowth on the area corresponding to the treatment area during that period. A photograph showing hair regrowth on the left side of a representative QLT 0074-treated mouse at day 17 is shown in FIG. 4. A mouse treated with placebo is shown in FIG. 3.

Similar results were obtained in another experiment in which mice were treated with the same formulation of 0.5% (w/w) QLT 0074, but a higher light dose of 150 J/ cm$^2$ was used.

EXAMPLE 3

Optimization of Irradiation Dose and Timing for Photodynamic Treatment of Alopecia Areata after Intravenous Injection of Photosensitizer This example examines the effect of different irradiation protocols on PDT treatment of alopecic mice as described above.

Alopecic mice are divided into control and treatment groups. The treatment mice are injected with verteporfin in a lipid-based formulation at 1 mg/kg of body weight, and the control group are mock injected. Mice from both groups are exposed to red light at the following doses: 1, 2, 5, 10 and 20 J/cm$^2$ light LED at 1 hour post-injection, in a manner as described above in Example 1. Two additional PDT treatments are administered on days 7 and 14 post photosensitizer administration. All mice are monitored over a 5 week period, photographed pre-treatment and on days 6, 13, 20, 27, and 34 post irradiation, and with biopsies taken for histopathological analysis.

In a separate experiment, alopecic mice are divided into control and treatment groups. The treatment mice are injected with verteporfin at 1 mg/kg of body weight, and the control group are mock injected. Mice from both groups are exposed to red light at 15 J/cm² light LED at 15, 30 and 60 120 and 180 minutes post-injection, in a manner as described above in Example 1. Two additional PDT treatments are administered on days 7 and 14 post photosensitizer administration. All mice are monitored over a 5 week period, photographed pre-treatment and on days 6, 13, 20, 27, and 34 post irradiation, and with biopsies taken for histopathological analysis.

EXAMPLE 4

Optimization of Drug Concentration, Irradiation Dose and Light Intensity on Hair Regrowth in Mice using Topically-applied QLT-0074

A study was performed to assess the effect of drug concentration (0.005, 0.05, or 0.5% QLT 0074 ointment), light dose (50, 100 or 150 J/cm² red light) and light intensity 50 or 200 mW/cm²) on hair regrowth in shaved female Balb/c mice. Mice received QLT 0074 ointment applied to the skin for 30 minutes, followed by a 15-minute treatment with placebo ointment and exposure to red light (688 nm). One group received no QLT 0074 ointment, only the placebo ointment and light exposure. Preparation of ointments and treatment procedure was as outlined in Example 2, except that different amounts of QLT 0074 were added.

Hair regrowth at the treatment site was observed in mice treated with a QLT 0074 ointment doses of 0.5% combined with light doses of 50, 100 or 150 J/cm² at 200 mW/cm². Hair regrowth at the treatment site was also observed for mice treated with 0.5% QLT 0074 ointment combined with either 50 or 100 J/cm² red light delivered at 50 mW/cm². Animals treated with 0.05% QLT 0074 ointment did not exhibit hair growth at any light dose, but hair regrowth at the treatment site was observed for one of three animals treated with 0.005% QLT 0074 ointment and 150 J/cm² delivered at 200 mW/cm². No hair regrowth occurred in mice that received placebo ointment only and were exposed to red light at 200 mW/cm².

Ointments were prepared as in Example 2, except that different amounts of QLT 0074 (on a weight/weight basis) were incorporated into the ointments. The treatment procedure was as outlined in Example 2.

Mild skin reactions were evident following some treatments, typically at the highest drug and light dose combinations, but no moderate or severe skin photosensitivity reactions were observed.

EXAMPLE 5

Stimulation of Hair Growth in Human Subjects with AGA

Subjects exhibiting hair loss associated with AGA were administered QLT 0074 in a topical ointment comprising 0.2% (weight/weight) of QLT 0074, and the other excipients outlined in Example 2. Approximately 224 mg of ointment was applied per 5.1 cm² of surface area, providing about 0.44 mg of QLT 0074/cm² of skin surface area. Application of QLT 0074 was localized to regions of the scalp exhibiting hair loss. The QLT 0074-containing ointment was left on for a period of either 30 minutes or two hours. After application, excess ointment was removed with a damp cloth. In some subjects, the vehicle ointment was applied to the treatment area for five minutes and then removed prior to irradiation. Irradiation was provided at a dose of 25, 50, 75 or 100 J/cm², administered at a fluence rate of 50 mW/cm². These irradiation doses required exposure of the skin for a duration of 8:20, 16:40, 25:00 and 33:20 (minutes:seconds), respectively. Light was delivered from a QB-Quanta_Med-688 nm Light Emitting Diode device.

EXAMPLE 6

Stimulation of Hair Growth in a Mouse Model of Alopecia Areata

A disease closely resembling human alopecia areata has been observed in aging (over 6-month old) C3H/HeJ mice ( see Sundberg, J. P et al, Alopecia Areata in Aging C3H/HeJ Mice, Journal of Investigative Dermatology 102(6): 847–856 [1994[). The C3H/HeJ mouse model has become recognized as a good model for the study of the etiology and pathogenesis of alopecia areata and for the evaluation of treatments for the disease (McElwee, K. J. et al, Comparison of Alopecia areata in Human and Nonhuman Mammalian Species, Pathobiology 66:90–107 (1998). A study was carried out to determine if topical application of QLT0074 ointment could influence hair re-growth on C3H/HeJ female mice exhibiting hair loss. The C3H/HeJ mice were obtained from the Jackson Laboratories, Bar Harbor, Me. Three animals received QLT0074 ointment, prepared as outlined in Example 2, at 0.2% (w/w) applied onto balding areas of skin, 1.5×1.5 cm in area. All other areas outside of the treatment site were left untreated.

Following this treatment, all 3 mice received a dose of 50 J/cm² 688 nm light delivered at a rate of 50 mw/cm² in the 1.5 square area. Mice were monitored for skin photosensitivity reactions on Days 1 and 3 after light exposure and observed for hair re-growth for up to 19 days post-treatment. With QLT0074 ointment and red light treatment, no skin photosensitivity reactions were observed for mice treated with light. At day 7 post-treatment, an increased amount of hair was observed in the treatment area of 2 of the 3 mice treated.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without undue experimentation. This application is intended to cover any variations, uses, or adaptations of the invention, following in general the principles of the invention, that include such departures from the present disclosure as come within known or customary practice within the art to which the invention pertains and as may be applied to the essential features hereinbefore set forth.

We claim:

1. A method of stimulating hair growth on the skin of a subject where hair loss has occurred, which method comprises
administering to the area of said skin where hair loss has occurred, an effective amount of a BPD or green porphyrin photosensitizer for penetrating into the area to result in a desired degree of biodistribution;

irradiating said area with light containing a wavelength of about 400 to about 900 nm and absorbed by said photosensitizer wherein hair growth is stimulated in said area.

2. The method of claim 1 wherein said hair growth reduction or hair loss is due to androgenetic alopecia, alopecia areata, drug-induced alopecia, or radiation induced alopecia.

3. The method of claim 1, wherein said subject is human.

4. The method of claim 1 wherein said effective amount of a photosensitizer is administered systemically at a dosage in the range of about 0.005 to about 10 mg/kg.

5. The method of claim 4 wherein said effective amount of a photosensitizer is administered systemically at a dosage in the range of about 0.005 to about 2 mg/kg.

6. The method of claim 1 wherein said effective amount of a photosensitizer is administered as an ointment containing about 0.001 to about 10% w/w photosensitizer.

7. The method of claim 6 wherein said effective amount of a photosensitizer is administered as an ointment containing about 0.005 to about 5% w/w photosensitizer.

8. The method of claim 7 wherein said effective amount of a photosensitizer is administered as an ointment containing about 0.05 to about 1% w/w photosensitizer.

9. The method of claim 8 wherein said effective amount of a photosensitizer is administered as an ointment containing about 0.2% w/w photosensitizer.

10. The method of claim 1 wherein said administration is intravenously, orally, subcutaneously, intramuscularly, intraperitoneally, intradermally, topically, or by use of an implant.

11. The method of claim 1 wherein the BPD is BPD-MA, EA6, or B3.

12. The method of claim 1 wherein irradiation delivers a total light dose of about 25, about 50, about 75, or about 100 $J/cm^2$.

13. The method of claim 1 wherein the time between said administering and irradiating is from about 5 minutes to about 6 hours.

14. The method of claim 13 wherein the time between said administering and irradiating is from about 30 to about 120 minutes.

15. The method of claim 1 wherein said administering and irradiating are repeated at least once.

16. A method of stimulating hair growth on the skin of an animal or human being where hair loss has occurred, which method comprises irradiating the area of said skin where hair loss has occurred, after contacting said area with an effective amount of a BPD or green porphyrin photosensitizer for penetrating into said area to result in a desired degree of biodistribution, with light containing a wavelength of about 400 to about 900 nm and absorbed by said photosensitizer wherein hair growth is stimulated in said area.

* * * * *